United States Patent [19]

Fontana et al.

[11] Patent Number: 4,499,273
[45] Date of Patent: Feb. 12, 1985

[54] SALTS OF AMINIC ORGANIC PEROXIDES

[76] Inventors: Alberto Fontana, 47, C. so Lodi;
Renzo Fontanelli, 19, Via Maiocchi;
Egeo Sacrini, 9, Via Campiglio;
Osvaldo Cicchetti, 57, Via Sapri, all
of Milano, Italy

[21] Appl. No.: 451,882

[22] Filed: Dec. 21, 1982

[30] Foreign Application Priority Data

Dec. 23, 1981 [IT] Italy .............................. 25822 A/81

[51] Int. Cl.³ ............................................ C07D 211/44
[52] U.S. Cl. ............................... 546/188; 260/239 A;
260/239 B; 260/239 BF; 524/581; 525/375;
525/437; 546/242; 548/556
[58] Field of Search ............................... 546/242, 188;
260/239 AR, 239 B, 239 BF; 548/556

[56] References Cited
FOREIGN PATENT DOCUMENTS 0056699 7/1982 European Pat. Off. ............ 546/242

Primary Examiner—Richard A. Schwartz

[57] ABSTRACT

There are disclosed new organic peroxides having two peroxy functional groups and containing in their molecule an atom of salified aminic nitrogen, having the general formula:

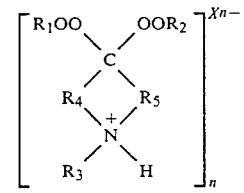

in which:

$R_1$, $R_2$ are each an alkyl radical having 1 to 8 carbon atoms, optionally aryl-substituted, preferably a tertiary alkyl group such as t.butyl, t.amyl, t.octyl and cumyl;

$R_3$ is a hydrogen, an alkyl radical having 1 to 8 carbon atoms, a cycloalkyl having 5-6 carbon atoms in the ring, an aryl, an arylalkyl optionally halogen, alkoxy-, carboalkoxy-, alkyl-, mono- or poly-substituted;

$R_4$ is the methylene, ethylene or trimethylene radical, optionally halogen-, alkoxy-, carboalkoxy-, aryl-, alkyl-, mono- or poly-substituted;

$R_5$ is the methylene or ethylene radical optionally halogen-, alkoxy-, carboalkoxy-, alkyl-, aryl-, mono- or poly-substituted;

X is an anion or an inorganic or organic acid in which one or more acid hydrogens are substituted by the aminic cation;

n is 1, 2 or 3 and represents the number of hydrogen atoms which are salified.

The peroxides so salified are employed in the crosslinking of plastomers, natural and synthetic elastomers and thermosetting resins.

This invention relates to salts of amino organic peroxides and, more particularly, to new organic peroxides having the peroxy functional groups, containing in their molecule an atom of salified aminic nitrogen, as well as to the use thereof in the cross-linking of plastomers, natural and synthetic elastomers and thermosetting resins.

10 Claims, No Drawings

SALTS OF AMINIC ORGANIC PEROXIDES

BACKGROUND OF THE INVENTION

It is known that the organic compounds of peroxide nature are particularly important as generators of free radicals and, in consequence, as starters of radicalic polymerizations, cross-linking agents for plastomers and vulcanizing agents for natural and synthetic elastomers.

However, not all the compounds of peroxide nature are employable in the cross-linking as a few types of peroxides are very difficult to treat owing to the tendency thereof to decompose, sometimes violently, at the temperature of use. Other peroxides have, at the temperature of incorporation into the polymer, a semi-lifetime which is so short that they cause a certain degree of undesirable pre-crosslinking during the mixing step.

THE PRESENT INVENTION

It is an object of the present invention to provide new peroxides endowed with a surprising stability and a low volatility.

We have found that such object is achieved by using peroxides having two peroxy functional groups and containing in the molecule an atom of salified aminic nitrogen.

Thus, it is an object of this invention to provide a new series of organic peroxides having two peroxy functional groups, containing in the molecule an atom of salified aminic nitrogen, and having the general formula:

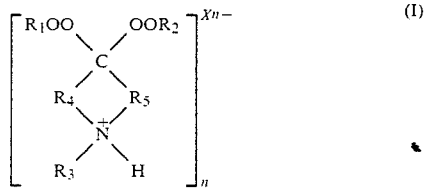

wherein:

$R_1$ and $R_2$ are each an alkyl radical having 1 to 8 carbon atoms optionally aryl-substituted, preferably a tertiary alkyl group such as t.butyl, t.amyl, t.octyl and cumyl;

$R_3$ is hydrogen, an alkyl radical containing 1 to 8 carbon atoms, a cycloalkyl containing 5-6 carbon atoms in the ring, an aryl, or an arylalkyl which is optionally halogen-, alkoxy-, carboalkoxy-, alkyl-mono- or poly-substituted;

$R_4$ is the methylene, ethylene, or trimethylene radical, optionally halogen-, alkoxy-, carboalkoxy- aryl-, or alkyl-mono- or poly-substituted;

$R_5$ is the methylene or ethylene radical, optionally halogen-, alkoxy-, carboalkoxy-, alkyl-, aryl- mono- or poly-substituted;

X is an anion of an organic or inorganic acid in which one or more acid hydrogens are substituted by the aminic cation; and n is 1, 2 or 3 and represents the number of hydrogen atoms which are salified.

Some examples of compounds falling within general formula (I) are the following:

(a) 4,4-di(t.butylperoxy)-2,2,6,6-tetramethylpiperidine formate,
(b) 4,4-di(t.butylperoxy)-2,2,6,6-tetramethylpiperidine acetate,
(c) 4,4-di(t.butylperoxy)-2,2,6,6-tetramethylpiperidine benzoate,
(d) 4,4-di(t.butylperoxy)-2,2,6,6-tetramethylpiperidine oxalate,
(e) 4,4-di(t.butylperoxy)-2,2,6,6-tetramethylpiperidine p-toluenesulphonate,
(f) 4,4-di(t.butylperoxy)-2,2,6,6-tetramethylpiperidine acid sulphate,
(g) 4,4-di(t.butylperoxy)-2,2,6,6-tetramethylpiperidine acid phosphate,
(h) 4,4-di(t.butylperoxy)-2,2,6,6-tetramethylpiperidine hydrochloride,
(i) 4,4-di(t.butylperoxy)-1,2,2,6,6-pentamethylpiperidine acid sulphate,
(l) 4,4-di(t.butylperoxy)-1,2,2,6,6-pentamethylpiperidine acid phosphate,
(m) 4,4-di(t.butylperoxy)-2,6-diphenylpiperidine acid sulphate,
(n) 4,4-di(t.butylperoxy)-2,6-diphenylpiperidine formate,
(o) 4,4-di(t.butylperoxy)-2,6-diphenylpiperidine benzoate,
(p) 4,4-di(t.butylperoxy)-2,6-diphenylpiperidine acid phosphate,
(q) 4,4-di(t.amylperoxy)-2,2,6,6-tetramethylpiperidine acid sulphate,
(r) 4,4-di(t.amylperoxy)-2,2,6,6-tetramethylpiperidine acetate,
(s) 4,4-di(cumylperoxy)-2,2,6,6-tetramethylpiperidine acid sulphate, and
(t) 1-benzyl-3,3-di(t.butylperoxy)-pyrrolidine acid sulphate.

The salified amino diperoxides according to the present invention exhibit a relatively high and differentiated decomposition temperature depending on the type of acid by which they have been salified. That permits the production, at moderate costs, of various peroxides derived from the same basic structure, operating in a relatively wide temperature range, thus allowing selection of the most suitable cross-linking and vulcanizing conditions in a given case.

Cross-linking is accomplished at a temperature of from 100° to 200° C., preferably from 140° to 170° C., at a pressure ranging from 50 to 200 kg/cm², in time periods of 5-60 minutes, preferably of 10-30 minutes. The weight concentration of the peroxide is comprised between 0.5 and 10%, preferably between 2 and 6% in respect of the plastomer.

Vulcanization is carried out at a temperature ranging from 140° to 190° C., preferably from 150° to 170° C., in time periods of 5-200 minutes, preferably of 5-30 minutes. The peroxide weight concentration is comprised between 0.5 and 10%, preferably between 2 to 6% in respect to the elastomer.

The mixtures having the following composition have proved particularly useful:

| | |
|---|---|
| Ethylene-propylene copolymer | 100 parts by weight |
| HAF carbon black | 20–80 parts by weight |
| ZnO (or MgO) | 1–10 parts by weight |
| Sulphur | 0.1–0.5 parts by weight |
| Peroxide | 0.005–0.02 mole. |

The hardening of an unsaturated polyester resin is accomplished at a temperature ranging from 50° to 170° C., preferably from 100° to 130° C. The peroxide concentration ranges from 0.01 to 5% by weight.

The diperoxides of the present invention are obtainable by various methods.

According to a presently preferred embodiment of this invention, the diperoxides are prepared by reacting an aminic organic diperoxide (described in the pending patent application of Renzo Fontanelli et al Ser. No. 338,906, filed Jan. 12, 1982) with an organic or inorganic acid.

Compositions comprising organic peroxides of the invention and plastomeric natural or synthetic resins, including thermosetting resins, may also comprise fillers and cross-linking co-agents.

For a more detailed discussion of the present invention and for the practice thereof, the following nonlimiting examples are given.

EXAMPLE 1

Preparation of 4,4-di(t.butylperoxy)-2,2,6,6-tetramethylpiperidine formate 31.7 g (0.1 mole) of 4,4-di(t.butylperoxy)-2,2,6,6-tetramethylpiperidine in 100 cc of hexane were introduced into a glass flask and 4.9 g (0.09 mole) of 85% formic acid were dropped in under stirring at room temperature. The resulting precipitate was filtered and washed with hexane.

After drying, 32 g of a white crystalline product were obtained which, on the basis of the centesimal analysis,

| % Found | % Calculated |
| --- | --- |
| C: 59.31 | 59.47 |
| H: 10.27 | 10.26 |
| N: 3.91 | 3.85 | was identified as 4,4-di(t.butylperoxy)-2,2,6,6-tetramethyl-piperidine formate having the following formula:

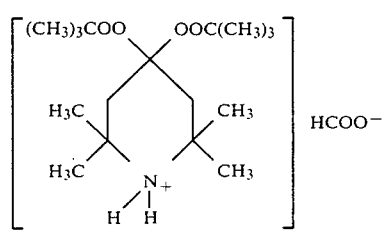

The melting and decomposition temperature of the product in a glass capillary was 152° C.

EXAMPLE 2

Preparation of 4,4-di(t.butylperoxy)-2,2,6,6-tetramethyl-piperidine acetate

Example 1 was repeated except that 5.4 g (0.09 mole) of glacial acetic acid, instead of the formic acid, were dropped into the flask under stirring at room temperature. The resulting precipitate was filtered and washed with hexane.

After drying, 33.5 g of a white crystalline product were obtained which, in the basis of the centesimal analysis,

| % Found | % Calculated |
| --- | --- |
| C: 60.31 | 60.45 |
| H: 10.41 | 10.41 |
| N: 3.62 | 3.71 | was identified as 4,4-di(t.butylperoxy)-2,2,6,6-tetramethylpiperidine acetate of formula:

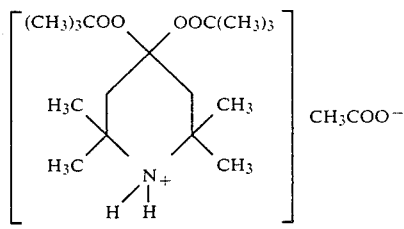

The melting and decomposition temperature of the product in a glass capillary was 149° C.

EXAMPLE 3

Preparation of 4,4-di(t.butylperoxy)-2,2,6,6-tetramethylpiperidine benzoate

Operating according to Example 1, a solution of 11 g (0.09 mole) of benzoic acid in 80 cc of ethyl ether was dropped under stirring at room temperature. The resulting precipitate was filtered and washed with hexane.

After drying, 38.5 g of a white crystalline product were obtained, which, on the basis of the centesimal analysis

| % Found | % Calculated |
| --- | --- |
| C: 65.44 | 65.57 |
| H: 9.40 | 9.40 |
| N: 3.11 | 3.18 | and of the I.R. analysis was identified as 4,4-di(t.butylperoxy)-2,2,6,6-tetramethylpiperidine benzoate having the formula:

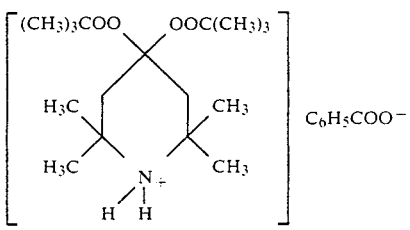

The melting and decomposition temperature of the product in a glass capillary was 178° C.

EXAMPLE 4

Preparation of 4,4-di(t.butylperoxy)-2,2,6,6-tetramethylpiperidine oxalate

Into a glass flask there were introduced 31.7 g (0.1 mole) of 4,4-di(t.butylperoxy)-2,2,6,6-tetramethylpiperidine in 100 cc of hexane. A solution of 5.7 g (0.045 mole) of dihydrated oxalic acid in 20 cc of methanol was then dropped in under stirring and at room temperature. The precipitate so obtained was filtered and washed with methanol.

After drying, 20 g of a white crystalline product were obtained, which, on the basis of the centesimal analysis

| % Found | % Calculated |
|---|---|
| C: 59.58 | 59.64 |
| H: 10.06 | 10.01 |
| N: 3.80 | 3.86 | was identified as 4,4-di(t.butylperoxy)-2,2,6,6-tetramethylpiperidine oxalate of formula:

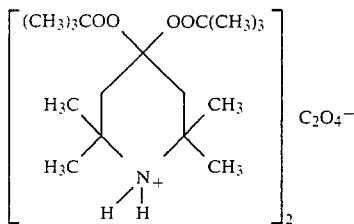

The melting and decomposition temperature of the product in a glass capillary was 155° C.

EXAMPLE 5

Preparation of 4,4-di(t.butylperoxy)-2,2,6,6-tetramethylpiperidine p-toluene sulphonate By operating as in the preceding examples, a solution of 17 g (0.09 mole) of monohydrated p-toluenesulphonic acid in 5 g of water was dropped under stirring at room temperature into a glass flask containing 31.7 g (0.1 mole) of 4,4-di(t.butylperoxy)-2,2,6,6-tetramethylpiperidine in 100 cc of hexane. The resulting precipitate was filtered and washed with 5 cc of water and successively with hexane.

After drying, 43 g of a white crystalline product were obtained, which, on the basis of the centesimal analysis

| % Found | % Calculated |
|---|---|
| C: 58.75 | 58.87 |
| H: 8.79 | 8.85 |
| N: 2.89 | 2.86 |
| S: 6.49 | 6.54 | and of the I.R. analysis, was identified as 4,4-di(t.butylperoxy)-2,2,6,6-tetramethylpiperidine p-toluenesulphonate having the formula:

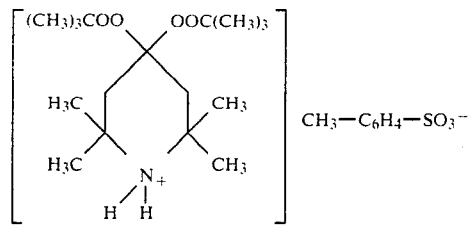

The melting and decomposition temperature of the product in a glass capillary was 167° C.

EXAMPLE 6

Preparation of 4,4-di(t.butylperoxy)-2,2,6,6-tetramethylpiperidine acid sulphate By operating as in the preceding examples, 24.4 g of an aqueous solution at 40% of sulphuric acid (0.1 mole) were dropped under stirring at room temperature into a glass flask containing 31.7 g (0.1 mole) of 4,4-di(t.butylperoxy)-2,2,6,6-tetramethylpiperidine in 100 cc of hexane. The resulting precipitate was filtered and washed with 5 cc of cold water and then with hexane.

After drying, 40 g of a white crystalline product were obtained, which, on the basis of the centesimal analysis

| % Found | % Calculated |
|---|---|
| C: 49.44 | 49.14 |
| H: 9.01 | 8.97 |
| N: 3.31 | 3.37 |
| S: 7.66 | 7.71 | was identified as 4,4-di(t.butylperoxy)-2,2,6,6-tetramethylpiperidine acid sulphate of formula:

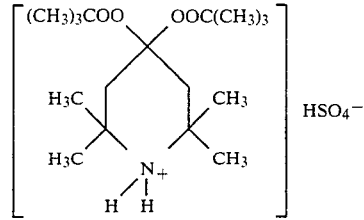

The melting and decomposition temperature of the product in a glass capillary was 153° C.

EXAMPLE 7

Preparation of 4,4-di(t.butylperoxy)-2,2,6,6-tetramethylpiperidine acid phosphate 10.4 (0.09 mole) of 85% phosphoric acid were dropped under stirring at room temperature into a glass flask containing 31.7 (0.1 mole) of 4,4-di(t.butylperoxy)-2,2,6,6-tetramethylpiperidine in 100 cc of hexane, as described in the preceding examples. The precipitate so obtained was filtered and washed with 5 cc of water, then with hexane.

After drying, there were obtained 36.5 g of a white crystalline product which, on the basis of the centesimal analysis

| % Found | % Calculated |
|---|---|
| C: 48.98 | 49.14 |
| H: 9.15 | 9.22 |
| N: 3.42 | 3.37 |
| P: 7.39 | 7.45 | was identified as 4,4-di(t.butylperoxy)-2,2,6,6-tetramethylpiperidine acid phosphate having the formula:

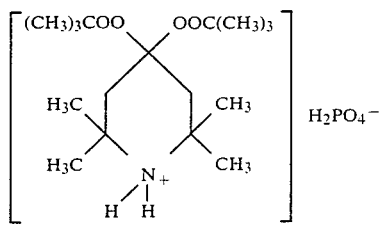

The melting and decomposition temperature of this product in a glass capillary was 172° C.

EXAMPLE 8

Preparation of 4,4-di(t.butylperoxy)-2,2,6,6-tetramethylpiperidine hydrochloride 31.7 g (0.1 mole) of 4,4-di(t.butylperoxy)-2,2,6,6-tetramethylpiperidine in 100 cc of hexane were introduced into a glass flask. 13.4 g of an aqueous solution at 25% of hydrochloric acid (0.09 mole) were then dropped in under stirring, at room temperature. The resulting precipitate was filtered and washed with 5 cc of cold water and successively with hexane.

After drying, 31.5 g of a white crystalline product were obtained, which on the basis of the centesimal analysis

| % Found | % Calculated |
|---|---|
| C: 57.77 | 57.68 |
| H: 10.29 | 10.25 |
| N: 3.89 | 3.96 |
| Cl: 10.04 | 10.01 | was identified as 4,4-di(t.butylperoxy)-2,2,6,6-tetramethylpiperidine hydrochloride of formula:

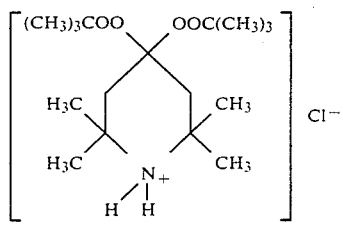

The melting and decomposition temperature of this product in a glass capillary was 170° C.

EXAMPLE 9

Preparation of 4,4-di(t.butylperoxy)-1,2,2,6,6-pentamethylpiperidine acid sulphate Into a glass flask there were introduced 34.9 g (0.1 mole) of 4,4-di(t.butylperoxy)-1,2,2,6,6-pentamethylpiperidine having a titer of 95% in 100 cc of hexane. Successively, 24.4 g of an aqueous solution at 40% of sulphuric acid (0.1 mole) were dropped in, under stirring, at room temperature. The resulting precipitate was filtered and washed with 5 cc of cold water and successively with hexane.

After drying, 42 g of a white crystalline product were obtained; such product was identified, on the basis of the centesimal analysis

| % Found | % Calculated |
|---|---|
| C: 50.29 | 50.34 |
| H: 9.13 | 9.15 |
| N: 3.22 | 3.26 |
| S: 7.51 | 7.46 | as 4,4-di(t.butylperoxy)-1,2,2,6,6-pentamethylpiperidine acid sulphate having the formula:

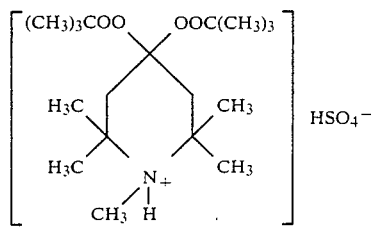

The melting temperature of said product in a glass capillary was 80° C. and the decomposition temperature was 100° C.

EXAMPLE 10

Cross-linking

The cross-linking tests were carried out on mixes based on polyethylene such as Fertene UK5-1830 (registered trademark of Montedison S.p.A.) having a density of 0.917 and a grade of 1.2 g/10 min. at 190° C. (ASTM D 1238), additioned with 0.01 mole of peroxide per 100 g of polyethylene.

The following Table 1 indicates the conditions under which the cross-linking was carried out and the cross-linking degree obtained by using the peroxide prepared according to Example 6 in comparison with 4,4-di(t.butylperoxy)-2,2,6,6-tetramethylpiperidine. The polyethylene cross-linking degree was measured by determining the solubility of the polymer in an organic solvent (decalin), according to the procedure fixed by method ASTM D 2765. The non-cross-linked polyethylene was completely soluble in the solvent.

TABLE 1
CROSS-LINKING

| Formulation | X | A | In the absence of peroxide |
|---|---|---|---|
| Low density polyethylene parts by weight | 100 | 100 | 100 |
| Peroxide moles parts by weight | 0.01 | 0.01 | — |
| Cross-linking in a press | 30 min. at 150° C. | 30 min. at 165° C. | — |
| Undissolved | 66.2 | 60 | fully |

TABLE 1-continued

CROSS-LINKING

| Formulation | X | A | In the absence of peroxide |
|---|---|---|---|
| polyethylene g/100 g | | | soluble |

Note
X = 4,4-di-t.butylperoxy-2,2,6,6-tetramethylpiperidine.
A = 4,4-di-t.butylperoxy-2,2,6,6-tetramethylpiperidine acid sulphate.

EXAMPLE 11

Vulcanization

The vulcanization tests were carried out on mixes based on ethylene-propylene copolymer DUTRAL CO 054 (registered trademark of Montedison S.p.A.) consisting for 55 mol % of ethylene—Mooney viscosity ML(1+4) at 100° C.=45.

Table 2 indicates the conditions under which vulcanization was carried out and the rheological and physical characteristics of the vulcanizates obtained by employing 4,4-di(t.butylperoxy)-2,2,6,6-tetramethylpiperidine acid sulphate, prepared in Example 6, in comparison with those of the vulcanizates obtained using the peroxide 4,4-di(t.butylperoxy)-2,2,6,6-tetramethylpiperidine.

TABLE 2

| FORMULATION | X | A |
|---|---|---|
| Dutral CO 054 parts by weight | 100 | 100 |
| Carbon black HAF parts by weight | 50 | 50 |
| ZnO parts by weight | 5 | 5 |
| S parts by weight | 0.3 | 0.3 |
| Mole of peroxide | 0.01 | 0.01 |
| Vulcanization in press | 20' at 150° C. | 30' at 165° C. |
| Initial characteristics: | | |
| Tensile strength kg/cm² | 204 | 190 |
| Elongation at break % | 263 | 315 |
| 200% modulus kg/cm² | 100 | 90 |
| Tear strength kg/cm | 37 | 40 |
| Shore A hardness | 70 | 70 |
| Characteristics after ageing in oven (7 days at 125° C.) | | |
| Tensile strength % | −3.6 | +14.8 |
| Elongation at break % | +12 | +14.4 |
| 200% modulus | −12 | −5 |
| Shore A hardness (variation in points) | +1 | +1 |
| Compression set % 70 h at 100° C. | 15 | 25 |
| Mooney scorch (t₁₀) min. | 6' | 45" |

X = 4,4-di(t.butylperoxy)-2,2,6,6-tetramethylpiperidine.
A = 4,4-di(t.butylperoxy)-2,2,6,6-tetramethylpiperidine acid sulphate.

EXAMPLE 12

Hardening of unsaturated polyester resins

The hardening tests of unsaturated polyester resins were carried out on a resin having the following composition:

| phthalic anhydride | 0.6 mole |
|---|---|
| maleic anhydride | 0.4 mole |
| propylene glycol | 1.05 moles |
| hydroquinone | 150 ppm |
| styrene | 36% referred to the finished product. |

Such resin, additioned with 1% of peroxide, was hardened at a temperature of 100° C. and 130° C.

Table 3 shows the time required to achieve the hardening of the resin for the following peroxides:

A: 4,4-di(t.butylperoxy)-2,2,6,6-tetramethylpiperidine acid phosphate
B: 4,4-di(t.butylperoxy)-2,2,6,6-tetramethylpiperidine p.toluenesulphonate
C: 4,4-di(t.butylperoxy)-2,2,6,6-tetramethylpiperidine oxalate
D: 4,4-di(t.butylperoxy)-2,2,6,6-tetramethylpiperidine benzoate
E: 4,4-di(t.butylperoxy)-2,2,6,6-tetramethylpiperidine acetate
F: 4,4-di(t.butylperoxy)-2,2,6,6-tetramethylpiperidine formate
G: 4,4-di(t.butylperoxy)-2,2,6,6-tetramethylpiperidine acid sulphate as compared with the peroxide
X: 4,4-di(t.butylperoxy)-2,2,6,6-tetramethylpiperidine.

TABLE 3

Hardening of Unsaturated Polyester Resins

| Peroxide | Hardening Time | |
|---|---|---|
| | at 130° C. | at 100° C. |
| A | 5.5 min. | 52 min. |
| B | 5 min. | 40 min. |
| C | 5 min. | n.d. |
| D | 5 min. | 35 min. |
| E | 4.7 min. | 36 min. |
| F | 4.5 min. | 28 min. |
| G | n.d. | 49 min. |
| X | 5 min. | 21 min. | n.d. = not determined.

We claim:

1. An organic peroxide having two peroxy functional groups, containing in the molecule thereof an atom of salified aminic nitrogen, and having the formula:

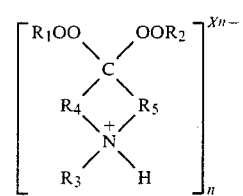

wherein:
R₁ and R₂ are each an alkyl radical selected from the group consisting of t.butyl, t.amyl, t.octyl and cumyl;
R₃ is hydrogen, an alkyl radical having 1 to 8 C, a cycloalkyl having 5–6 carbon atoms in the ring, or an aryl radical selected from the group consisting of the phenyl and benzyl radicals;
R₄ is the methylene, ethylene or trimethylene radical, at least mono-substituted by methyl or phenyl;
R₅ is the methylene or ethylene radical at least mono-substituted by methyl or phenyl;
X is an anion of an inorganic or organic acid in which one or more acid hydrogens are substituted by the aminic cation; and
n is 1, 2 or 3 and represents the number of hydrogen atoms which are salified.

2. An organic peroxide according to claim 1, and which is 4,4-di(t.butylperoxy)-2,2,6,6-tetramethylpiperidine formate.

3. An organic peroxide according to claim 1, and which is 4,4-di(t.butylperoxy)-2,2,6,6-tetramethylpiperidine acetate.

4. An organic peroxide according to claim 1, and which is 4,4-di(t.butylperoxy)-2,2,6,6-tetramethylpiperidine benzoate.

5. An organic peroxide according to claim 1, and which is 4,4-di(t.butylperoxy)-2,2,6,6-tetramethylpiperidine oxalate.

6. An organic peroxide according to claim 1, and which is 4,4-di(t.butylperoxy)-2,2,6,6-tetramethylpiperidine p-toluenesulphonate.

7. An organic peroxide according to claim 1, and which is 4,4-di(t.butylperoxy)-2,2,6,6-tetramethylpiperidine acid sulphate.

8. An organic peroxide according to claim 1, and which is 4,4-di(t.butylperoxy)-2,2,6,6-tetramethylpiperidine acid phosphate.

9. An organic peroxide according to claim 1, and which is 4,4-di(t.butylperoxy)-2,2,6,6-tetramethylpiperidine hydrochloride.

10. An organic peroxide according to claim 1, and which is 4,4-di(t.butylperoxy)-1,2,2,6,6-pentamethylpiperidine acid sulphate.

* * * * *